(12) United States Patent
Sater

(10) Patent No.: US 7,942,301 B2
(45) Date of Patent: May 17, 2011

(54) VASCULAR PUNCTURE STAPLING SYSTEM

(75) Inventor: Ghaleb Sater, Acton, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 660 days.

(21) Appl. No.: 12/104,812

(22) Filed: Apr. 17, 2008

(65) Prior Publication Data

US 2009/0264923 A1    Oct. 22, 2009

(51) Int. Cl.
*A61B 17/064* (2006.01)
(52) U.S. Cl. .................................. 227/175.1; 606/219
(58) Field of Classification Search ............... 227/175.1, 227/179.1, 19, 901, 902; 606/138, 142, 151, 606/153, 219–221; 411/457, 459, 920
See application file for complete search history.

(56) References Cited

U.S. PATENT DOCUMENTS

| | | | |
|---|---|---|---|
| 4,610,251 A | 9/1986 | Kumar | |
| 6,348,064 B1 * | 2/2002 | Kanner | 606/219 |
| 6,506,210 B1 * | 1/2003 | Kanner | 606/213 |
| 6,533,762 B2 * | 3/2003 | Kanner et al. | 604/175 |
| 6,645,205 B2 * | 11/2003 | Ginn | 606/41 |
| 6,719,767 B1 * | 4/2004 | Kimblad | 606/151 |
| 6,767,356 B2 * | 7/2004 | Kanner et al. | 606/213 |
| 7,074,232 B2 | 7/2006 | Kanner et al. | |
| 7,597,706 B2 * | 10/2009 | Kanner et al. | 606/219 |
| 2004/0093024 A1 * | 5/2004 | Lousararian et al. | 606/213 |
| 2006/0217744 A1 * | 9/2006 | Bender et al. | 606/142 |
| 2007/0233187 A1 * | 10/2007 | Lobello | 606/219 |

* cited by examiner

*Primary Examiner* — Paul R Durand
*Assistant Examiner* — Andrew M Tecco

(57) ABSTRACT

A stapling system includes a tissue staple, a mandrel, and a pusher. The staple includes a crown at the proximal end and a plurality of prongs extending distally therefrom about a central axis of the staple. Each prong of the staple includes a tab extending towards the central axis. The mandrel receives the staple along an outer surface thereof. The mandrel includes a proximal groove adapted to receive the tab of the corresponding prong. The proximal groove includes a ramp from a proximal portion of the proximal groove to a distal portion of the proximal groove. The mandrel further includes a distal groove adapted to receive the tabs of the prongs and a distal anvil disposed distally of the distal groove. The pusher is disposed around the mandrel abutting and proximal to crown of the staple.

10 Claims, 5 Drawing Sheets

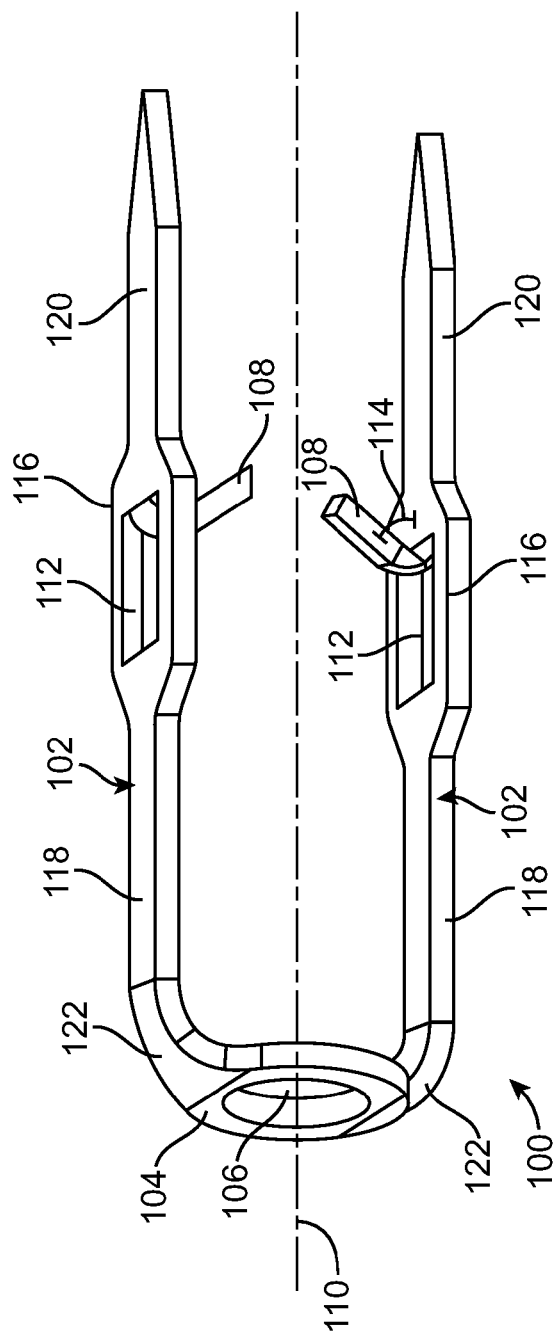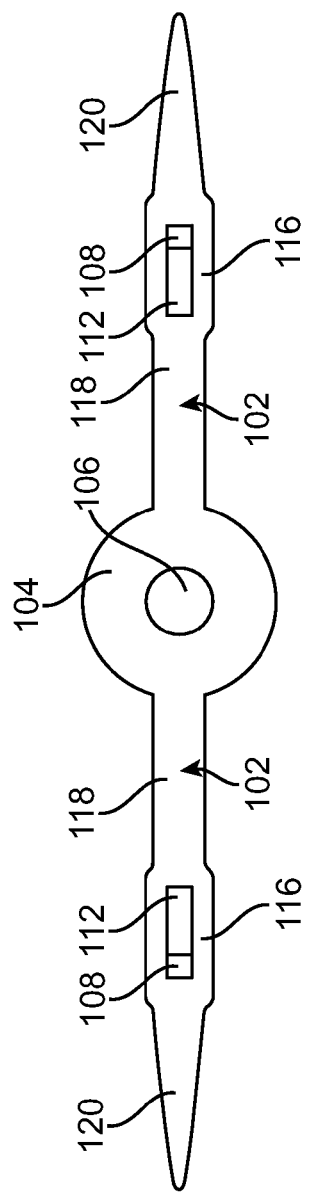

VASCULAR PUNCTURE STAPLING SYSTEM

FIELD OF THE INVENTION

The present disclosure relates to systems and methods for closing an opening in a vessel wall after a medical procedure, and in particular, to a system and method for closing a puncture arteriotomy after an intra-luminal procedure such as catheterization.

BACKGROUND OF THE INVENTION

Various cardiovascular procedures, such as angioplasty, stent placement and atherectomy, require inserting into and manipulating within the vasculature, wires and catheters adapted to perform those procedures. Access to the vasculature typically is through the femoral artery and is percutaneous, involving insertion of a needle in the region of the groin to form a track through subcutaneous tissue and to puncture and create an arteriotomy in the femoral artery. A short guidewire is then advanced through the needle and into the femoral artery. The needle then is removed. An introducer sheath is then advanced over the guidewire, along the track and into the femoral artery. The introducer sheath provides access into the femoral artery, through the arteriotomy, for catheters or other instrumentalities in order to perform the selected procedure.

After the procedure has been completed, the procedural devices are removed and the arteriotomy must be closed. The size of the puncture opening in the artery corresponds to the size of the catheter or percutaneous introducer sheath used, which devices may typically range in diameter from 5 French (1.67 mm) for a diagnostic procedure to 6-10 French (2.00 mm-3.33 mm) for a therapeutic procedure. A number of techniques are known to facilitate closure and healing of the arteriotomy. One technique includes application of pressure at the puncture site for a relatively extended length of time. More particularly, compression has traditionally been applied to the puncture site for at least 30-45 minutes for the wound to close naturally after removal of the catheter. Patients are required to remain decumbent, essentially motionless and often with a heavy sandbag placed on their upper leg, for several hours to ensure that clot has formed at the arteriotomy to prevent bleeding. The recovery time from the medical procedure may be as little as half of an hour, but the recovery time from the wound can exceed 24 hours. This makes wound site management the longer critical care item. The longer the recovery time, the more expensive the procedure becomes, the greater the patient discomfort, and the greater the risk of complications.

Also among the techniques for closing the arteriotomy is the use of a staple system such as described in U.S. Pat. Nos. 6,506,210, 6,767,356 and 7,074,232 to Kanner et al., the disclosures of which are incorporated by reference herein in their entirety. The Kanner patents describe a system by which the original introducer sheath is removed, leaving the guidewire in place. An assembly that includes a closure sheath and dilator is then advanced along the indwelling guidewire to bring the distal end of the sheath into proximity to the arteriotomy. The closure sheath also carries, at its distal end, an arrangement of wire-like stabilizers that, together with the dilator, pass through the arteriotomy into the artery. The system enables the portions of the stabilizer wires disposed within the artery to be formed into a temporarily enlarged shape that prevents removal of the wires through the arteriotomy and holds the sheath in place. The stabilizers and distal end of the sheath are drawn together to grip the tissue about the arteriotomy and thereby secure and fix the position of the distal end of the sheath over and in alignment with the arteriotomy. The dilator and guidewire then can be removed through the sheath, leaving the closure sheath in place adjacent the outer surface of the artery with the stabilizers within the artery, in place in readiness to provide direct access to the arteriotomy through the sheath.

A catheter-like stapling device, with a staple carried in its distal end, then is advanced through the closure sheath to locate the staple in proximity to the arteriotomy. As described more fully in the Kanner patents, the stapler and sheath include mechanisms by which the staple, when advanced through the sheath, will be oriented in registry with and at a fixed distance from the arteriotomy. When the stapler is actuated, the prongs of the staple first expand and advance toward and into the arterial wall on opposite sides of the arteriotomy. Continued operation of the stapling mechanism draws the prongs of the staple together to draw the edges of the arteriotomy together into approximation and then releases the staple. The stabilizers return to a low profile shape enabling their withdrawal from the artery. With the staple deployed and having closed the arteriotomy the stapling mechanism and sheath may be removed, leaving the staple in place. The invention herein provides a staple and stapling system that are simpler and less expensive to manufacture than previously known staples and stapling systems.

SUMMARY OF THE INVENTION

A tissue staple includes a crown at the proximal end and a plurality of prongs extending distally from the crown. The prongs are disposed about a central axis of the staple. Each prong of the staple includes a tab extending towards the central axis. Each prong may include a widened portion where the tab is located and an opening configured to receive the tabs when they are bent proximally during deployment of the staple.

A stapling system includes the staple, a mandrel, and a pusher. The mandrel receives the staple along an outer surface thereof. The mandrel includes a proximal groove corresponding to each prong. The proximal groove is adapted to receive the tab of the corresponding prong. The proximal groove includes a ramp from a proximal portion of the proximal groove to a distal portion of the proximal groove where the ramp meets the outer surface of the mandrel. The mandrel further includes a distal groove adapted to receive the tabs of the prongs and a distal anvil disposed distally of the distal groove. The distal groove and distal anvil form an abrupt angle. The pusher is disposed around the mandrel and proximal to the staple such that a distal end of the pusher abuts the crown of the staple.

In a method for closing a vascular puncture, the mandrel, the pusher, and the staple are advanced to the region of the vascular puncture. Relative movement between the pusher and the mandrel advance the staple such that the tabs of the prongs ride along the ramps of the proximal grooves to splay the prongs. Further distal advancement of the staple causes the prongs to pierce tissue around the vascular puncture. After piercing the tissue, further relative movement between the mandrel and the staple is caused such that the tabs of the prongs elastically close into the distal groove. The mandrel is then withdrawn proximally such that the tabs abut the abrupt angle between the distal groove and the distal anvil, causing the prongs to deform towards the central axis, the tabs to bend proximally to clear the distal anvil, and the staple to release from the mandrel.

DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is isometric illustration of a two prong staple according to an embodiment of the present invention.

FIG. 2 is top view of the staple of FIG. 1 flattened out.

DESCRIPTION OF THE ILLUSTRATIVE EMBODIMENTS

Figure 3:
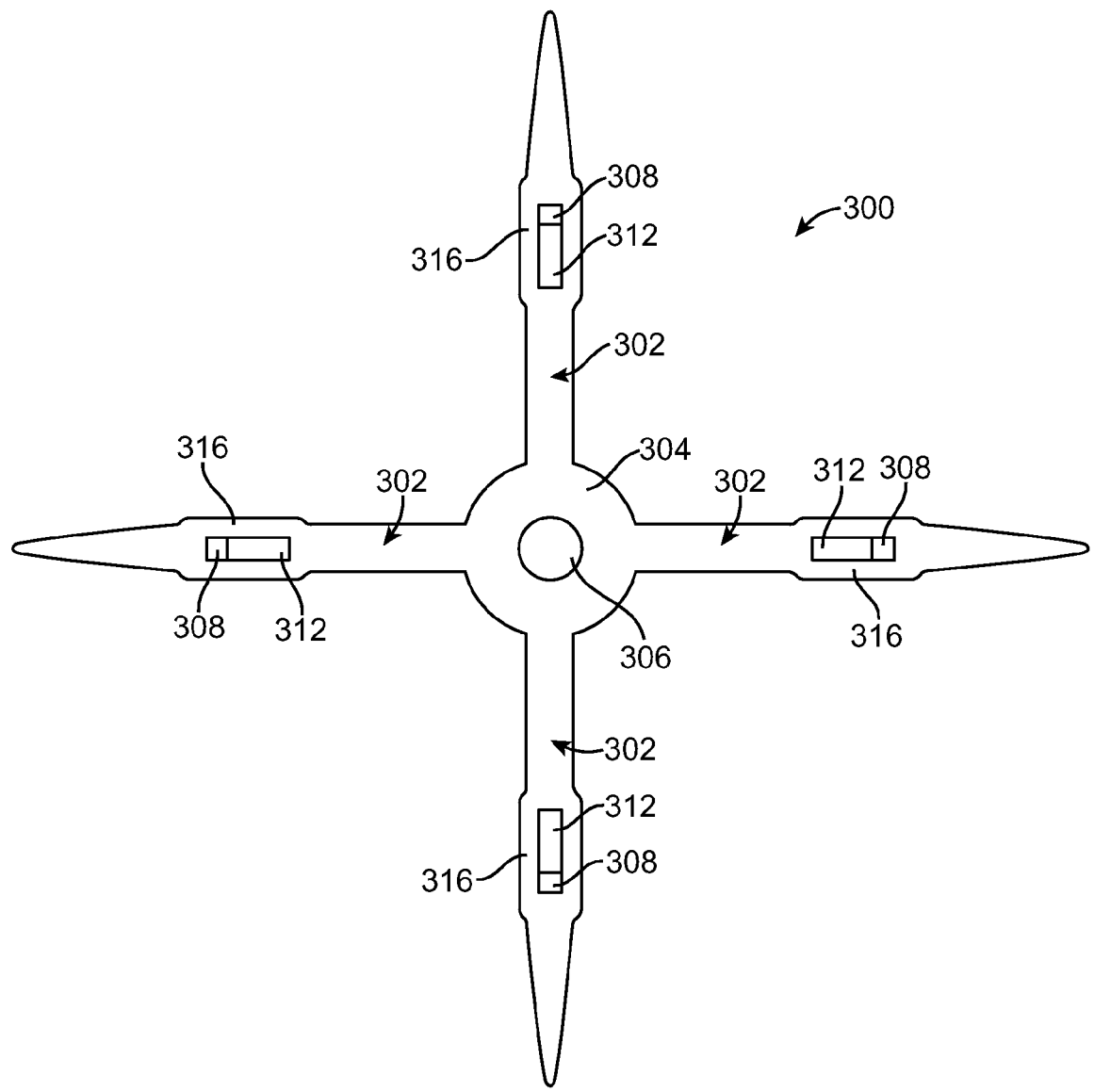
FIG. 3 is a flattened out top view of a staple including four prongs.
Figure 4:
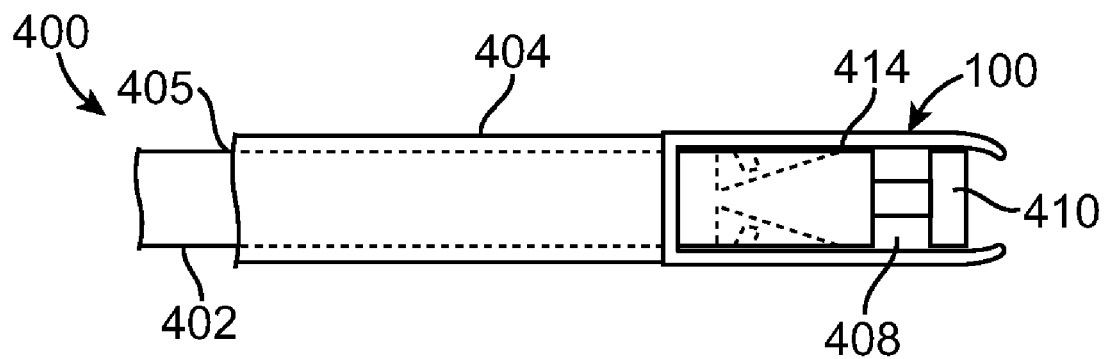
FIG. 4 is an elevation or side view of a stapling system according to an embodiment of the present invention.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

FIG. 1 is an isometric illustration of a staple 100 in accordance with an embodiment of the present invention. Staple 100 is provided to close a puncture in an artery or vein following a diagnostic or interventional catheterization procedure. However, it should be apparent to those of ordinary skill in the art that staple 100 may be used for general tissue repair, not just limited to vascular repair. Staple 100 comprises a pair of prongs 102 and a crown region 104 coupling the proximal ends of the prongs 102 together. Crown region 104 includes an opening 106 disposed there through. In the present embodiment, opening 106 is circular, but it may be other shapes. Each prong 102 includes a tab 108 extending toward an imaginary axis 110 of staple 100 disposed between prongs 102. In the embodiment of FIG. 1, an end of each tab 108 is coupled to its respective prong 102. Further, an opening 112 through the respective prong 102 is approximately the size of tab 108 such that tab 108 may rest within opening 112 when bent to a position substantially parallel to the prong, as explained in more detail below. Further, each tab 108 extends toward axis 110 and distally away from crown region 104 such that an angle 114 between tab 108 and prong 102 distal of tab 108 is less than 90 degrees. Each prong 102 further includes a widened region 116 at tab 108. Widened region 116 is provided such that opening 112 may be provided through prong 102 while maintaining structural integrity the prong. Instead of a through opening 112, an indentation or groove may be provided in each prong 102 from which the tabs 108 extend. The tabs may then be bent back into the groove, as described in more detail below. Alternatively, tabs 108 may extend from prongs 102 without an opening 112 (or groove) or widened region 116 such that tabs 108 may be bent back into an abutting relationship with prongs 102.

Prongs 102 each include a proximal prong portion 118 disposed proximal of tab 108 and a distal prong portion 120 disposed distal of tab 108. A shoulder 122 couples proximal prong portion 118 of each prong 102 to crown region 104. In the embodiment of FIGS. 1 and 2, shoulder 122 is a bend in the proximal end of prong 102.

Staple 100 may be constructed out of a spring-type metal such as stainless steel or titanium, or a superelastic metal such as nickel-titanium (nitinol). FIG. 2 shows a staple blank efficiently formed as a sheet-metal stamping from that may be formed into staple 100. FIG. 2 shows a two prong arrangement, as shown in FIG. 1, with prongs 102 arranged diametrically opposite each other. In FIG. 2, tabs 108 have been stamped, punched, bent or attached such that tabs 108 project from prongs 102 at angle 114, as shown in FIG. 1. Finally, the staple blank is formed into staple 100 by bending the prongs 102 to extend in the distal direction, generally parallel to the central axis 110 of the staple 100.

Although FIGS. 1 and 2 depict staple 100 having two prongs 102, this should only be considered exemplary. Staple 100 may include more than two prongs. For example, and not by way of limitation, FIG. 3 shows a staple blank of a staple 300 including four prongs 302. Each prong 302 is equally spaced around a crown region 304. Crown region 304 includes an opening 306. Each prong 302 includes an opening 312 through a widened region 316, and a tab 308 for extending towards an imaginary axis of staple 300 when in a finished form (not shown), as in the two prong embodiment shown in FIG. 1. The staple could alternatively include three prongs, five prongs or more prongs distributed equally around and extending from a crown, each with a corresponding tab.

FIGS. 4-11 illustrate a stapling system 400 and a method for deploying a staple. As would be understood by those of ordinary skill in the art, stapling system 400 is advanced through a tissue track (not shown) to the site of a vascular puncture 504. Stapling system 400 may be advanced through the tissue track to the region of the puncture without a delivery sheath and/or stabilizing device, for example, over a guidewire. Alternatively, stapling system 400 may be advanced to the region of the puncture through a delivery sheath and/or stabilizing device in order to facilitate tracking of the staple deployment system to the region of the puncture. For example, and not by way of limitation, the staple deployment system of the present invention may be advanced through a delivery sheath and stabilizing device of the type described in the Kanner patents listed above. As described in the Kanner patents, wire-like stabilizers extend through a delivery sheath. The distal ends of the stabilizers are configured to be placed through the vascular puncture into the lumen of a vessel. The stabilizers, which are inserted in a linear configuration, then are actuated into an enlarged configuration, so that they resist being withdrawn through the vascular puncture. The stabilizers and the delivery sheath provide a stable delivery platform held in a centered position over the region of the vascular puncture. The staple delivery system of the present invention may be inserted through the delivery sheath and advanced to the region of the vascular puncture. Reference is made to the Kanner patents for additional details concerning various constructions and embodiments of the delivery sheath and stabilizing system, which are incorporated by reference herein, in their entirety.

Figure 5:
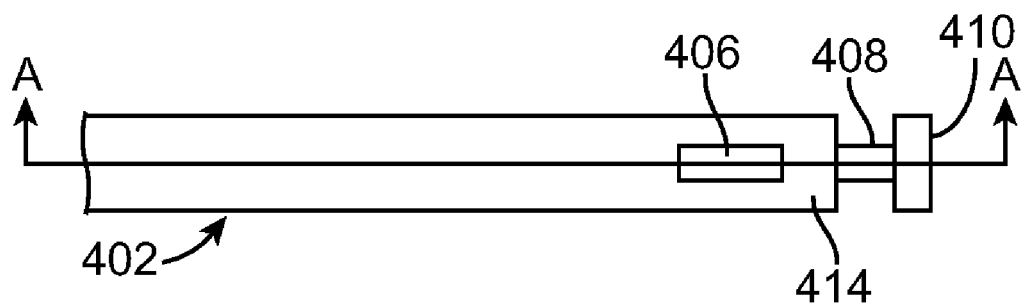
FIG. 5 is a top view of a mandrel of the staple deployment system of FIG. 4.
Figure 6:
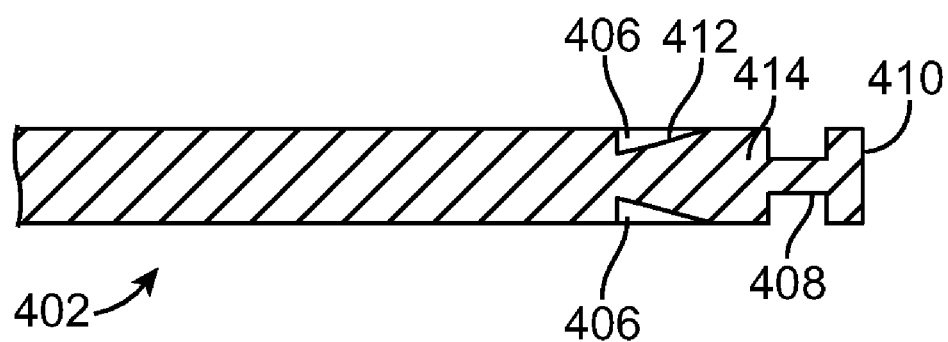
FIG. 6 is longitudinal sectional view of the mandrel of FIG. 5 taken along line A-A.

Referring back to FIGS. 4-6, stapling system 400 includes a mandrel 402 and a pusher 404 slidably mounted thereabout. Pusher 404 is a hollow tube with a lumen 405. Mandrel 402 is disposed within lumen 405 of pusher 404. FIGS. 5 and 6 illustrate mandrel 402 without pusher 404 or staple 100. FIG. 5 illustrates a top view of mandrel 402 and FIG. 6 is a sectional view taken along line A-A of FIG. 5. A distal region of mandrel 402 includes two proximal grooves 406 arranged diametrically opposite each other. Mandrel 402 is designed for staple 100 including two prongs 102 and two tabs 108. One of ordinary skill in the art would recognize that a mandrel for use with a staple including more prongs and tabs would include a corresponding number of proximal grooves. For example, a mandrel for use with staple 300 including four prongs 302 and four tabs 308 would include four grooves equally spaced around the mandrel. Similarly, a mandrel for use with a staple including three prongs or five prongs would include three proximal grooves or five proximal grooves, respectively. Alternatively, a single proximal groove 406 that extends circumferentially around mandrel 402 may be used, similar to distal groove 408 described in more detail below. Each proximal groove 406 includes a ramp 412 such that a proximal portion of proximal groove 406 is deeper than a distal portion of proximal groove 406, which meets with an outside surface of mandrel 402 at an expander portion 414.

Distal of expander portion 414 is a distal groove 408. In the embodiment shown in FIGS. 4-11, distal groove 408 extends around the circumference of mandrel 402. A distal anvil 410 is located distal of distal groove 408. Whereas proximal groove 406 includes a ramp 412 leading to expander portion 414, distal groove 408 and distal anvil 410 intersect at an abrupt angle. In the embodiment shown, distal groove 408 and distal anvil 410 intersect at a perpendicular angle.

Figure 7:
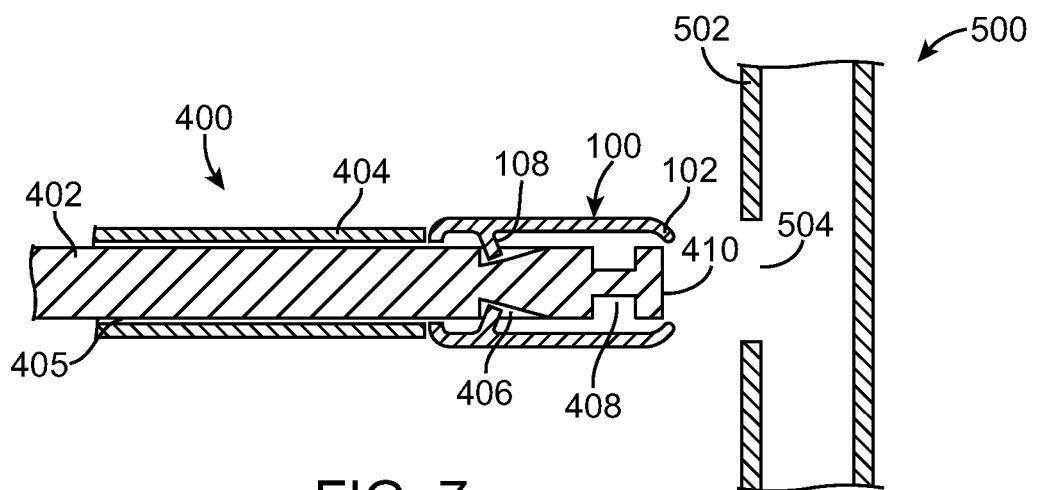
FIGS. 7-11 are longitudinal sectional views of the stapling system of FIG. 4 illustrating delivery of the staple around a vascular puncture.

FIGS. 7-11 illustrate deployment of staple 100 from stapling system 400. Stapling system 400 is advanced through the tissue track (not shown) to a position proximal of vascular puncture 504 in a vessel 500. System 400 is advanced through the tissue track with prongs 102 of staple 100 disposed substantially parallel to each other and to axis 110, as shown in FIG. 7. Further, tabs 108 are disposed within respective proximal grooves 406.

Figure 8:
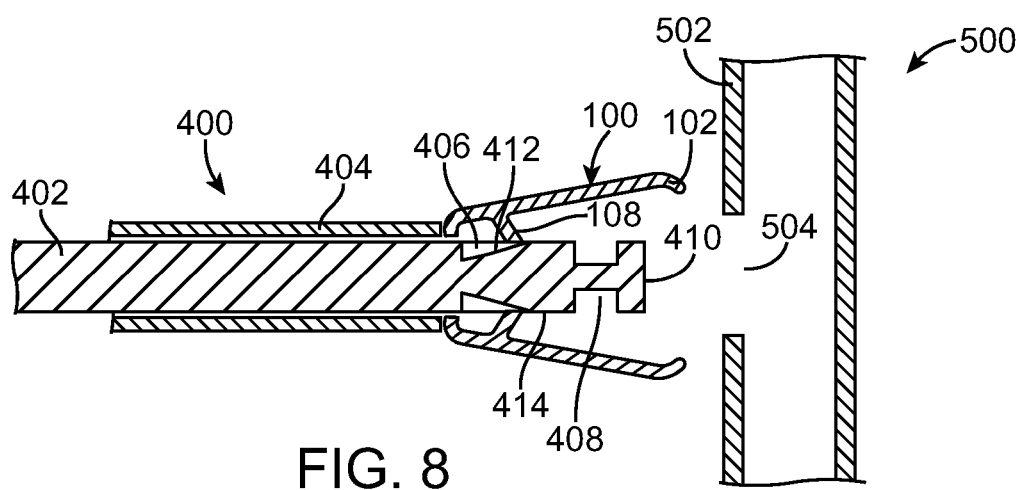

Upon reaching a predetermined distance from the vascular puncture 504, mandrel 402 and pusher 404 are moved relative to each other such that staple 100 slides distally with respect to mandrel 402, as shown in FIG. 8. As staple 100 moves distally with respect to mandrel 402, tabs 108 slide along ramps 412 and onto expander portion 414, thereby causing prongs 102 to splay apart from each other. The sharp distal tips of prongs 102 are radially spread apart because the proximal ends of prongs 102 are fixed to crown 106 and can only bend with respect thereto. Prongs 102 splay elastically. It is advantageous to splay prongs 102 prior to insertion into tissue 502 surrounding vascular puncture 504 such that the splayed prongs 102 can grasp a large portion of tissue 502 around the puncture site. The relative movement between mandrel 402 and pusher 404 to splay prongs 102 may be executed by moving mandrel 402 proximally while maintaining pusher 404 in a static position, moving pusher 404 distally while maintaining mandrel 402 in a static position, or a combination of moving mandrel 402 proximally and moving pusher 404 distally. The manner in which the relative movement is executed may generally be selected based on the predetermined distance from the vascular puncture site such that staple 100 will be advanced into the tissue 502 surrounding vascular puncture 504 with prongs 102 splayed apart from each other. If system 400 is relatively close to the vascular puncture site, proximal movement of mandrel 402 is preferred. If system 400 is advanced such that system 400 is relatively farther from the vascular puncture site, distal movement of pusher 404 is preferred in order to advance staple 100 adjacent to the tissue 502 surrounding vascular puncture 504.

Figure 9:
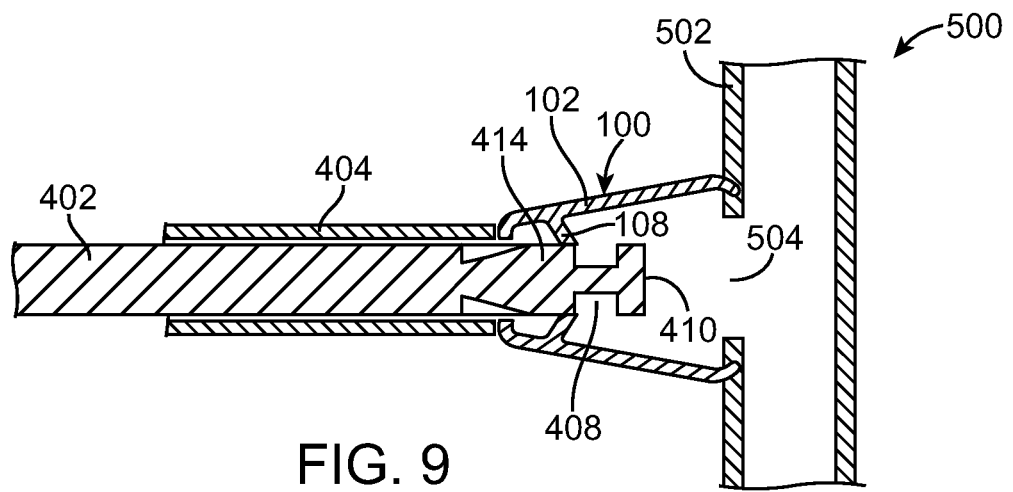

After staple 100 is advanced distally with respect to mandrel 402 to splay prongs 102, pusher 404 is advanced further distally with respect to mandrel 402, as shown in FIG. 9. This distal movement of pusher 404 causes staple 100 to advance distally. Tabs 108 of staple 100 ride along expander portion 414 such that prongs 102 remain splayed as prongs 102 advance into tissue 502 surrounding the vascular puncture 504. FIG. 9 shows staple 100 as tabs 108 reach a distal end of expander portion 414.

Figure 10:
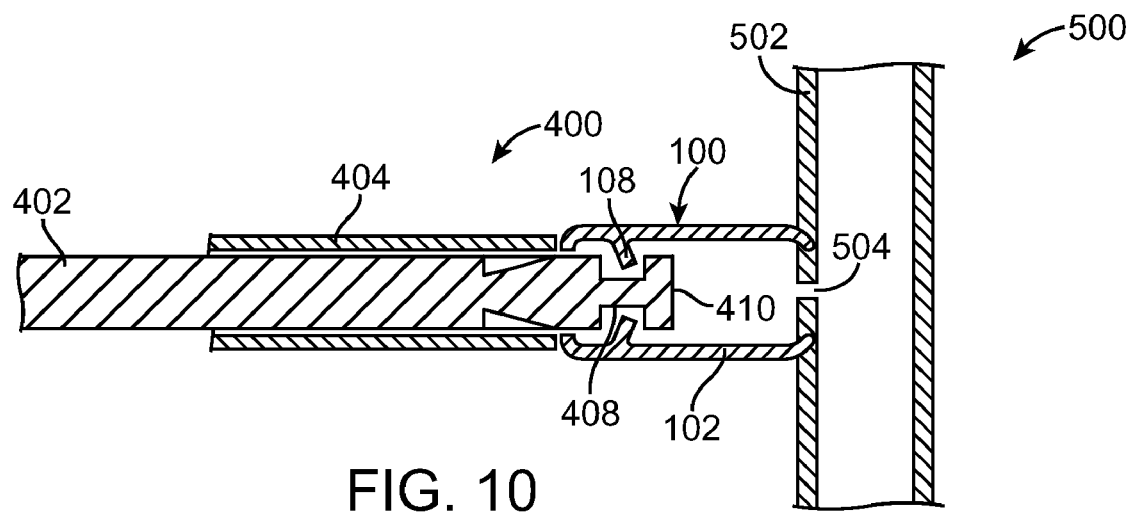

After staple 100 has been advanced to the distal end of expander portion 414, further relative movement between mandrel 402 and pusher 404 causes staple 100 to move distally relative to mandrel 402 such that tabs 108 reach distal groove 408. As tabs 108 reach distal groove 408, the retained elasticity of staple 100 causes prongs 102 to move towards each other and axis 110, as shown in FIG. 10. Although FIG. 10 shows prongs 102 generally parallel to each other and to axis 110, similar to the configuration shown in FIG. 7, one of ordinary skill in the art would recognize that varying the depth of distal groove 408 relative to proximal groove 406 may result in prongs 102 moving closer towards each other when tabs 108 reach distal groove 408. Also, the depth to which tabs 108 enter distal groove 408 may be determined by the amount of vessel tissue 502 gathered between prongs 102 and the physical properties of that tissue.

After prongs 102 have been advanced into the tissue 502 surrounding the vascular puncture 504 and prongs 102 have closed towards each other, further relative movement between mandrel 402 and pusher 404 causes staple 100 to move distally with respect to mandrel 402. Preferably, this relative movement is executed by withdrawing mandrel 402 proximally such that staple 100 does not advance further into tissue 502 surrounding the vascular puncture 504. As mandrel 402 is withdrawn proximally, distal anvil 410 encounters tabs 108. Due to the abrupt angle between distal groove 408 and distal anvil 410, a proximal force acts on tabs 108 of staple 100. Staple 100 is formed such that this force causes proximal prong portion 118 of each prong 102 to bend away from axis 110, which causes distal prong portion 120 of each prong to bend towards axis 110. Prongs 102 are plastically deformed such that the sharp distal tips are directed radially inward towards axis 110 to gather and hold closed the vascular tissue 502 surrounding the vascular puncture 504.

Figure 11:
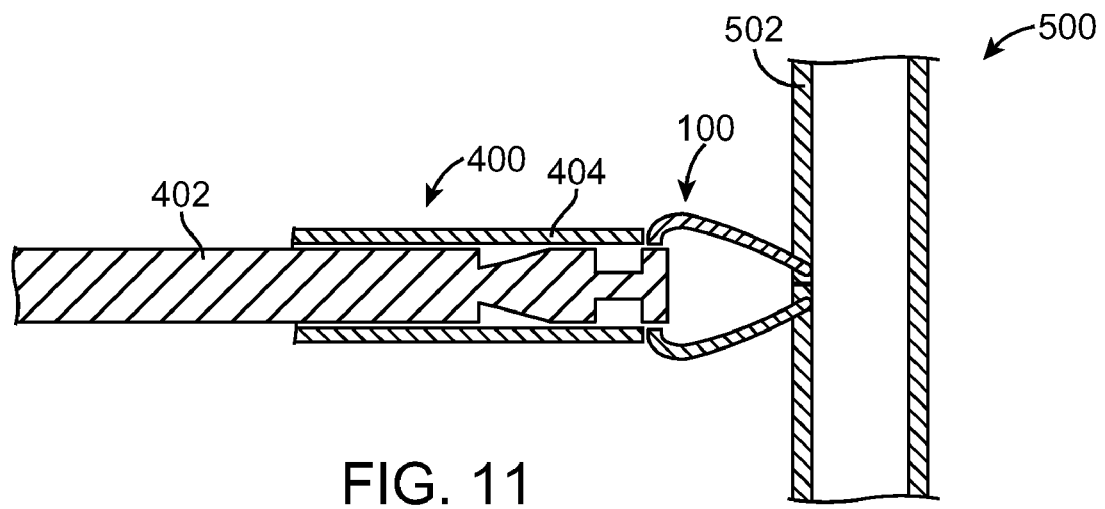

As mandrel 402 continues to be withdrawn proximally, the force on tabs 108 causes tabs 108 to bend proximally. Openings 112 in prongs 102 are sized to receive tabs 108, such that tabs 108 bend into openings 112. Accordingly, as mandrel 402 is withdrawn proximally, distal prong portions 120 close towards each other and tabs 108 bend proximally to allow staple 100 to slide off of mandrel 402, thereby releasing staple 100 from staple deployment system 400. As shown in FIG. 11, distal anvil 410 and opening 106 in staple 100 are sized such that staple 100 will slide off of mandrel 402 as mandrel 402 is withdrawn proximally. When staple 100 is released from mandrel 402, staple deployment system 400 is removed from the tissue track, leaving staple 100 in place surrounding the vascular puncture.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stapling system for closing a vascular puncture comprising:
    a tissue staple having proximal and distal ends with a crown at the proximal end and a plurality of prongs extending distally from the crown, the staple having a central axis and the prongs being disposed about the central axis, wherein each prong includes a tab extending towards the central axis;
    a mandrel adapted to slidably receive the staple along an outer surface of the mandrel, the mandrel including,
        a proximal groove corresponding to each prong, the proximal groove adapted to receive the tab of the corresponding prong,
        a ramp disposed within each proximal groove,
        a distal groove disposed distal of the ramp, wherein the distal groove is adapted to receive the tabs of the prongs, and
        a distal anvil disposed distally of the distal groove, wherein the distal groove and the distal anvil form an abrupt angle; and
    a pusher adapted to slidably receive the mandrel within a lumen of the pusher, wherein the pusher is disposed proximally of the staple and a distal end of the pusher is abuts the crown of the staple.

2. The stapling system of claim 1, wherein the ramp is configured such that the tab of the corresponding prong rides along the ramp upon distal movement of the staple relative to the mandrel to splay the prongs of the staple.

3. The stapling system of claim 2, wherein the staple is configured such that when the tabs reach the distal groove upon further distal movement of the staple relative to the mandrel, the prongs elastically move towards the center axis as the tabs enter the distal groove.

4. The stapling system of claim 3, wherein the prongs are configured to plastically deform such that prong distal tips are directed towards the central axis upon distal movement of the tabs against the abrupt angle between the distal groove and the distal anvil.

5. The stapling system of claim 4, wherein the tabs are configured to bend proximally during or after the prong distal tips are deformed towards the central axis in response to a force of the tabs against the abrupt angle.

6. The stapling system of claim 1, wherein each tab forms an angle of less than 90 degrees with a portion of the corresponding prong distal of the tab.

7. The stapling system of claim 1, wherein staple includes two prongs and the mandrel includes two proximal grooves.

8. The stapling system of claim 1, wherein the staple includes four prongs and the mandrel includes four proximal grooves.

9. The stapling system of claim 1, wherein each prong includes a widened portion and the corresponding tab of each prong is coupled to the prong at the widened portion.

10. The stapling system of claim 9, wherein the widened portion includes an opening disposed through the widened portion and the tab is coupled to the widened portion at a distal end of the opening.

* * * * *